US011313859B2

(12) United States Patent
Richter Dahlfors et al.

(10) Patent No.: US 11,313,859 B2
(45) Date of Patent: Apr. 26, 2022

(54) DETECTION OF MICROBIAL PEPTIDES

(71) Applicant: Richter Life Science Development AB, Saltsjö-Boo (SE)

(72) Inventors: Agneta Richter Dahlfors, Saltsjö-Boo (SE); Andrew Benjamin Libberton, Stockholm (SE); Peter Nilsson, Linköping (SE); Marcus Bäck, Linköping (SE); Susanne Löffler, Älta (SE); Hamid Shirani Bidabadi, Bandhagen (SE); Xiankeng Choong, Sundbyberg (SE); Charalampos Antypas, Solna (SE)

(73) Assignee: RICHTER LIFE SCIENCE DEVELOPMENT AB, Saltsjo-Boo (SE)

( * ) Notice: Subject to any disclaimer, the term of this patent is extended or adjusted under 35 U.S.C. 154(b) by 0 days.

(21) Appl. No.: 15/764,735

(22) PCT Filed: Sep. 28, 2016

(86) PCT No.: PCT/SE2016/050919
§ 371 (c)(1),
(2) Date: Mar. 29, 2018

(87) PCT Pub. No.: WO2017/058085
PCT Pub. Date: Apr. 6, 2017

(65) Prior Publication Data
US 2018/0275125 A1    Sep. 27, 2018

(30) Foreign Application Priority Data
Oct. 1, 2015 (SE) .................... 1551259-3

(51) Int. Cl.
| | | |
|---|---|---|
| *G01N 33/569* | (2006.01) | |
| *G01N 33/58* | (2006.01) | |
| *C07D 333/10* | (2006.01) | |
| *G16B 40/00* | (2019.01) | |
| *G16B 40/30* | (2019.01) | |
| *G16H 10/40* | (2018.01) | |
| *G06F 17/18* | (2006.01) | |
| *G06F 16/00* | (2019.01) | |

(52) U.S. Cl.
CPC ..... *G01N 33/56911* (2013.01); *C07D 333/10* (2013.01); *G01N 33/582* (2013.01); *G06F 17/18* (2013.01); *G16B 40/00* (2019.02); *G16B 40/30* (2019.02); *G16H 10/40* (2018.01); *G06F 16/00* (2019.01); *Y02A 50/30* (2018.01); *Y02A 90/10* (2018.01)

(58) Field of Classification Search
CPC ....... C07D 333/10; G06F 17/18; G06F 16/00; G16B 40/00; G16B 40/30; G16H 10/40; Y02A 50/30; Y02A 90/10
See application file for complete search history.

(56) References Cited

U.S. PATENT DOCUMENTS

| | | | |
|---|---|---|---|
| 6,841,669 B2 | 1/2005 | Cipriani et al. | |
| 9,958,439 B2* | 5/2018 | Richter Dahlfors | ... G01N 33/50 |
| 2001/0026915 A1 | 10/2001 | Charych et al. | |
| 2013/0196872 A1* | 8/2013 | Low | ........................ B03C 5/005 |
| | | | 506/9 |
| 2014/0135322 A1 | 5/2014 | Asberg et al. | |
| 2014/0273000 A1 | 9/2014 | Stys et al. | |
| 2018/0245089 A1* | 8/2018 | Sharei | ................ C12N 15/8206 |

FOREIGN PATENT DOCUMENTS

| | | |
|---|---|---|
| WO | WO-02081735 A2 | 10/2002 |
| WO | WO-03029479 A2 | 4/2003 |
| WO | WO-2010044744 A1 | 4/2010 |
| WO | WO-2011039535 A2 | 4/2011 |
| WO | WO-2011102789 A1 | 8/2011 |
| WO | WO-2013036196 A1 | 3/2013 |
| WO | WO-2013158550 A1 | 10/2013 |
| WO | WO-2014007730 A1 | 1/2014 |
| WO | WO-2014125321 A1 | 8/2014 |
| WO | WO-2014/138919 A1 | 9/2014 |

OTHER PUBLICATIONS

Klingstedt T. et al., "Luminescent Conjugated Oligothiophenes for Sensitive Fluorescent Assignment of Protein Inclusion Bodies", 2013 Wiley-VCH Verlag GmbH& Co. KGaA, Weinheim, ChemBioChem 2013, 14, 607-616.

Klingstedt T. et al., "Luminescent Conjugated poly- and oligothiophenes: optical ligands for spectral assignment of a plethora of protein aggregates", Biochemical society Transactions (2012) vol. 40, part 4.

Nilsson K. P. R. et al., "A Pentameric Luminescent-Conjugated Oligothiophene for Optical Imaging of In Vitro-Formed Amyloid Fibrils and Protein Aggregates in Tissue Sections", Einar M. Sigurdsson et al. (eds.), Amyloid Proteins: Methods and Protocols, Methods in Molecular Biology, vol. 849, DOI 10.1007/978-1-61779-551-0_29, © Springer Science+Business Media, LLC 2012.

Bjork P. et al., "Dynamics of complex formation between biological and luminescent conjugated polyelectrolytes—a surface plasmon resonance study", Biosensors and Bioelectronics 20 (2005) 1764-1771.

(Continued)

*Primary Examiner* — Tracy Vivlemore
*Assistant Examiner* — Nam P Nguyen
(74) *Attorney, Agent, or Firm* — James S. Keddie; Bozicevic, Field & Francis LLP (57) ABSTRACT

The present invention relates to a method for detection, identification, and/or quantification of one or more microbes, microbial peptides, or compounds of microbial origin, comprising the steps of: (a). contacting an object, a substance, or a sample with a luminescent conjugated oligothiophene (LCO); (b). detecting at least one signal of the luminescent conjugated oligothiophene (LCO) of a); and (c). based on said at least one detected signal in b), determining the presence, identity, and/or quantity of the one or more microbes, microbial peptides, or compounds of microbial origin on said object or in said sample. The present invention further relates to diagnostics and a method of diagnosis of microbes, microbial peptides, or compounds of microbial origin.

20 Claims, 5 Drawing Sheets

(56) References Cited

OTHER PUBLICATIONS

Kai-Larsen Y. et al., "Uropathogenic *Escherichia coli* Modulates Immune Responses and Its Curli Fimbriae Interact with the Antimicrobial Peptide LL-37", PLoS Pathogens | www.plospathogens.org, Jul. 2010 | vol. 6 | Issue 7 | e1001010.

Solano et al, "Discrimination of Strains of *Salmonella enteritidis* with Differing Levels of Virulence by an In Vitro Glass Adherence Test", Virulence Discrimination of S. Enteritidis Strains, vol. 36, 1998.

Latasa et al., "BapA, a large secreted protein required for biofilm formation and host colonization of *Salmonella enteric* serovar Enteritidis", Molecular Microbiology (2005) 58 (5), 1322-1339, First published online Oct. 14, 2005.

Slund et al., "Novel Pentameric Thiophene Derivatives for in Vintro and in Vivo Optical Imaging of a Plethora of Protein Aggregates in Cerebral Amyloidoses," ACA Chemical Biology, vol. 4, No. 8, Aug. 21, 2009, pp. 673-684.

Plante et al., "Polythiophene Biosensor for Rapid Detection of Microbial Particles in Water," ACS Applied Materials & Interfaces, vol. 5, No. 11, Jun. 12, 2013, pp. 4544-4548.

Nasser et al., "Polymer dots for quantifying the total hydrophobic pathogenic lysates in a single drop," Colloids and Surfaces. B, Biointerfaces, vol. 115, No. 4, Nov. 20, 2013, pp. 51-60.

Baek et al., "Design and Synthesis of Novel Glycopolythiophene Assemblies for Colorimetric Detection of Influenza Virus and *E.coli*", Bioconjug Chem., vol. 11, Issue 6, pp. 777-788, 2000.

Plante et al., "Polythiophene Biosensor for Rapid Detection of Microbial Particles in Water", ACS Applied Materials & Interfaces, vol. 5, Issue 11, pp. 4544-4548, 2013.

Abdelhamid et al., "Polymer Dots for Quantifying the Total Hydrophobic Pathogenic Lysatesin a Single Drop", Colloids and Surfaces B: Biointerfaces, vol. 115, pp. 51-60, 2014.

Ma et al., "Glycosylation of Quinone-Fused Polythiophene for Reagentless and Label-Free Detection of *E.coli*", Analytical Chemistry, vol. 87, Issue 3, pp. 1560-1568, 2015.

Wankar et al., "Polythiophene Nanofilms for Sensitive Fluorescence Detection of Viruses in Drinking Water", Biosensors and Bioelectronics, vol. 82, pp. 20-25, 2016.

International Search Report dated Mar. 16, 2017 for PCT Application No. PCT/SE2016/050919.

\* cited by examiner

DETECTION OF MICROBIAL PEPTIDES

FIELD OF THE INVENTION

The present invention relates to a method for detection, identification, and quantification of microbes, microbial peptides or compounds of microbial origin, enabling diagnostics and diagnosis of an infection.

TECHNICAL BACKGROUND

Biological macromolecules are grouped in classes as Proteins, Carbohydrates, Nucleic acids and Lipids. Each class is chemically and structurally distinct, and performs unique functions essential to life. Proteins are composed of amino acids, which linked to each other via peptide (amide) bonds forms a polymeric chain. The primary sequence is organised in higher tiers of complexity resulting in secondary, tertiary, and eventually quarternary structures, which refers to the number and the arrangement of aggregated protein subunits with respect to one another. Short chains of amino acid monomers linked by peptide bonds are termed peptides. Peptides produced by microbes are termed microbial peptides. Carbohydrates are primarily composed of carbon, hydrogen and oxygen atoms. Based on their degree of polymerization, carbohydrates can be classified as sugars, oligosaccharides and polysaccharides. Nucleic acids, such as DNA and RNA, are composed of nucleotide monomers, each consisting of a sugar, a phoshphate group, and a nitrogenous base. Lipids are molecules that, in contrast to the macromolecules mentioned above, are soluble in organic solvents. Lipids are the main components in biological membranes, such as the plasma membrane enveloping cells.

Microbes can produce all classes of molecules mentioned above. Some serves as targets for methods aiming for microbe identification. Antibodies identify microorganisms based on their protein composition, whereas lectins identify carbohydrates. Methods involving polymerase chain reaction (PCR) and next generation sequencing can identify microorganisms based on the sequence of nucleic acids. These methodologies do not overlap owing to the difference in chemical composition and structure of each molecular class.

Figure 7:
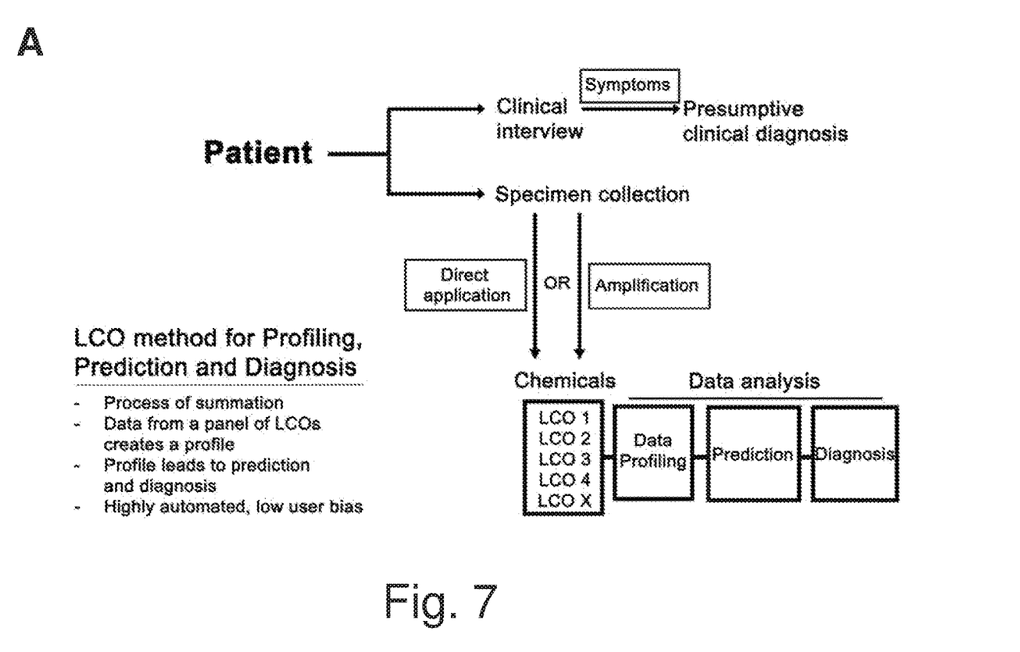

Microbes express a wide range of molecules on their outer surface for a variety of functions. These molecules may function as structural components for stability, colonisation or surface adhesion, enzymatic reactions, immune evasion, molecule transport, etc. Diagnosis of disease caused by microbes and identification thereof in diseases typically takes a minimum of 2 to 3 days by traditional microbiological methods (FIG. 7B). Diagnosis of infection requires a composite of findings based on patient history, patient examination and laboratory data. Isolation of the microorganism from the clinical sample for diagnosis is a difficult task. In cases when the microbe can be isolated and amplified to sufficient quantities, the microbe is subjected to an extensive battery of biochemical tests. Elimination and exclusion of results leads eventually to the identification of the causative agent. Commonly used biochemical tests pertain to the presence of specific enzymes, indicative of well-known pathogens. However, the test is often not definitive. Physicians are obliged to treat patients with generic protocols and wide spectrum acting drugs, which drives the development of antibiotic resistance, and can cause other complications. Research has shown this to be a highly detrimental approach. Many methods for diagnosis are only useful for organisms that are possible to cultivate, which is time consuming and expensive. Methods and techniques are required to reduce the time and improve the accuracy of diagnosis and indirectly control the cost of treatment. The methods need to be simple and rapid.

Luminescent Conjugated Oligothiphenes (LCOs) are a group of fluorophores that experience a change in molecule geometry when interacting with a target. Target binding induces a change in fluorescence signal, producing an optical signature that is unique to the target. In some cases, this optical signal is either ON/OFF and in other cases the signal can be a change in excitation and/or emission spectra or signal intensity. LCOs have been used or proposed to be used in various different domains. Most of the work has been carried out to use LCOs as markers and imaging agent. Klingstedt et al (Klingstedt T, Blechschmidt C, Nogalska A, Prokop S, Häggqvist B, Danielsson O, Engel W K, Askanas V, Heppner F L, Nilsson K P. Chembiochem. 2013; 14(5): 607-16. doi:10.1002/cbic.201200731) describes use of LCOs for detection of inclusion proteins, while Klingstedt and Nilsson (Klingstedt T, Nilsson K P. Biochem Soc Trans. 2012; 40(4):704-10. doi: 10.1042/BST20120009) illustrates use of luminescent conjugated poly- and oligo-thiophenes for imaging of protein aggregates.

Nilsson et al (Nilsson K P, Lindgren M, Hammarström P. Methods Mol Biol. 2012; 849:425-34. doi: 10.1007/978-1-61779-551-0_29) has used a pentameric LCO as an anionic probe for protein aggregate staining. US20140273000 provides for a method of detecting a disease associated with abnormal protein aggregation using p-FTAA or a luminescent conjugated polythiophene (LCP) or LCO related to p-FTAA that shall bind to protein aggregates (β-amyloid, α-synuclein, huntingtin, tau protein, hyperphosphorylated tau protein (pTau), prion protein, αB-crystallin (CRYAB), desmin, selenoproteins, actin and/or myosin), while WO2014125321 relates to multimodal agents for imaging LCO (q-FTAA) conjugated to magnetic nanoparticles for detection for misfolded proteins. WO2013036196 relates to thiophene compounds for use in imaging amyloid deposits and aggregated protein in living patients and US2014135322 relates to thiophene compounds as therapeutic compositions for treatment of diseases caused by misfolded or aggregated proteins. As can be seen, the above publications and patent applications relate to identification or treatment of misfolded proteins or aggregated proteins.

U.S. Pat. No. 6,841,669 provides functionalized thiophene oligomers as fluorescent markers for proteins, polyclonal antibodies or monoclonal antibodies or both, and their fractions, nucleic acids, oligonucleotides, hormones, medicines, drugs, and non-proteic chemical neurotransmitters. Bjork et al developed a biosensor based on a water-soluble polythiophene, POWT, with zwitterionic peptide like side chains for the detection of DNA and antibody antigen interaction. (Björk P, Persson N K, Nilsson K P R, Åsberg P, Inganäs O. Biosens Bioelectron. 2005; 20(9):1764-71). Similarly WO2011102789 describes oligothiophene derivatives that bind specifically to neural stem cells and neural cancer stem cells, however the patent application does not detail out the component to which the oligothiophene is binding.

WO2010044744 relates to novel substituted thiophene derivatives useful in imaging of amyloid deposits and aggregated protein in living patients. It also extends to some non-disease amyloids that are native amyloids in organisms, such as yeast prions (Sup35), *Podospora anserina* prion (Het-s), *E. coli* protein (curlin), malarial coat protein, spider silk, mammalian melanosomes (pMel), tissue-type plasminogen activator (tPA), calcitonin and proteins and peptides engineered to make amyloid. WO2014007730 discloses a method for detecting carbohydrates with LCOs, however WO2014007730 does not provide any method of infection diagnosis. None of the above mentioned publications or patent applications are providing solutions for identification of microbial peptides or diagnosis based on microbial peptide or carbohydrate based structures.

The present invention intends to overcome the above mentioned disadvantages by using specific LCOs for accurate detection and quantification of microbial targets through a rapid and easy method. This invention fills a novel gap in knowledge not identified in WO2010044744 where LCOs target amyloid proteins only. The use of LCOs on non-amyloid targets is not trivial and a novel area identified in this present invention. In WO2014007730 is disclosed a method for detecting carbohydrates with LCOs, however WO2014007730 does not mentioned the detection of microbial proteins or peptides. Owing to the distinctly different chemical composition and structures of the amino acid-containing proteins/peptides and sugar-containing carbohydrates, its is unexpected for LCOs to be applicable to proteins/peptides. The method according to the present invention will also reduce the costs associated with diagnosis and treatment with respect to the conventional methods that depend on constant expression of microbial factors over several days of testing for detection thereof. The method according to the present invention also presents novel binding targets which can be used to detect specific bacterial components.

SUMMARY OF THE INVENTION

One aim of the present invention is to provide a method for detection of microbial peptides, microbes or compounds of microbial origin. Another objective of the invention is to provide a method to identify microbial peptides, microbes or compounds of microbial origin. Yet another objective of the invention is to provide a method for diagnosis of microbes, microbial peptides or compounds of microbial origin from any samples. Still another objective of the invention is to provide a method for quantification of microbial peptides, microbes or compounds of microbial origin. Another objective of this invention is to provide an interface enabling detection or identification or diagnosis or quantification of microbes, microbial peptides or compounds of microbial origin.

The purpose above is achieved by a method for detection, identification, and/or quantification of one or more microbes, microbial peptides, or compounds of microbial origin, comprising the steps of:
(a). contacting an object, a substance or a sample with a LCO;
(b). detecting at least one signal of the LCO of a); and
(c). based on said detected signal in b), determining the presence, identity, and/or quantity of the one or more microbial peptides or microbes on said object or in said sample.

There are several advantages with the present invention and among those providing a method that enables identification of microbial peptides and microbes with ease, that reduces time of detection and diagnosis, that provides a method to identify uncultivable bacteria and that further provides analysis methods reducing the subjectivity aspect of diagnosis.

SHORT DESCRIPTION OF THE DRAWINGS

FIG. 7: LCO method for profiling, prediction and diagnosis (FIG. 7A) and Traditional method for diagnosis (FIG. 7B).

DETAILED DESCRIPTION

Below, specific embodiments of the present invention are described. In one embodiment the present invention is a method for detection, identification, and/or quantification of one or more microbes, microbial peptides, or compounds of microbial origin, comprising the steps of:
(a). contacting an object, a substance, or a sample with a LCO;
(b). detecting at least one signal of the LCO of a); and
(c). based on said detected at least one signal in b), determining the presence, identity, and/or quantity of the one or more microbial peptides, microbes or compounds of microbial origin on said object or in said substance or sample.

In one embodiment the above method can also be used for identification of microbes and microbial peptides and for diagnostics of infection. In another aspect, the invention therefor relates to a method for the diagnosis of an infection and identification of causative microbes producing one or more microbes, microbial peptides or compounds of microbial origin comprising the steps of:
(a'). contacting an object, a substance, or a sample with a LCO;
(b'). detecting at least one signal of the LCO of a'); and
(c'). comparing said detected at least one signal obtained in b') with a database, wherein said database comprises data from detected signals of previously known samples of microbial peptides.

In one embodiment the present invention is a method for detection, identification, and/or quantification of microbial peptides. In one embodiment the present invention is a method for detection, identification, and/or quantification of microbes. In one embodiment said microbial peptide has been bound to or is in contact with a microbe, a microbial peptide or compound of microbial origin which LCO binding or contact produces a unique signal that can be compared to a database for identification and diagnosis. In one embodiment the unique signal produced is produced due to LCO binding. In another embodiment the luminescent conjugated oligothiophene (LCO) has been bound to or is in contact with a microbe, microbial peptide or compound of microbial origin which produce a unique signal that can be compared to a database for identification and diagnosis of infection.

In one embodiment the database comprises data from samples earlier obtained of at least one microbe, microbial peptide, or compound of microbial origin, wherein said data comprises detection signals of said samples earlier obtained of at least one microbe, microbial peptide, or compounds of microbial origin. In one embodiment compounds of microbial origin may be microbial carbohydrates. Preferably said data is an average of more than one sample earlier obtained or data of a single sample. Said data may be a compilation of more than one sample earlier obtained or data of a single sample. In another embodiment the database comprises data in both raw and analyzed forms that has been organized and/or presented for systematic comparison or storage. The data may be illustrated or analyzed using ratio analysis or multivariate analysis, e.g. cluster analysis, principle component analysis (PCA), factor analysis, and hierarchical clustering. The data may also be illustrated or analyzed using more complex machine learning approaches such as linear discriminant analysis. In another embodiment the method of the present invention, further comprises the steps:
(a"). comparing said at least one detected signal of the sample, object or substance to a database comprising data of detected signals of known samples;
(b"). statistical analysis of said detected signal in relation to data of previous samples in said database; and
(c"). identification and/or quantification based on results obtained from step (b").

Any of the steps of said method can be carried out in vitro, in vivo or in situ and can be carried out sequentially or continuously. These steps can be manual or automated. In one embodiment at least step a), and/or step b) is or are carried out in vivo, in vitro or in situ. In another embodiment at least step a'), and/or step b') is or are carried out in vivo, in vitro or in situ. In another embodiment at least step a"), and/or step b") is or are carried out in vivo, in vitro or in situ. And in yet another embodiment at least one or all steps is or are carried out in vivo, in vitro or in situ.

In said method the object substance or sample may be from human, animal, or environmental origin, or obtained from an object that may be 'stand-alone' or has been placed in interaction with a subject of human, animal, biological or environmental origin, which is further put in contact with the LCO that is either freely available in a solution or attached to a surface. In one embodiment said object, substance or sample/samples earlier obtained is/are of human, animal, biological or environmental origin. In another embodiment said object, substance or sample/samples earlier obtained is/are from an object, preferably said object may be 'stand-alone' or has been placed in interaction with a subject of human, animal, biological or environmental origin. For example, a sample could originate from an object in a body such as an implant. The samples, substances or objects may be further processed to collect or remove attached LCOs.

The LCOs used according to the present invention range in length from tetrameric to dodecameric and preferably are pentameric or heptameric in length. In one embodiment said LCO is a tetrameric to dodecameric LCO. In another embodiment said LCO is a tetrameric to 15-meric LCO. In another embodiment said LCO is a pentameric or heptameric LCO. One embodiment comprises a mixture of different of lengths.

The LCOs can according to the present invention be modified with side chains selected from the group comprising of such as but not limited to carboxylic acids, acetic acids, propionic acids, amino acids, amino acid derivatives, neurotransmitters, monosaccharides, polysaccharides, nucleic acids and derivatives as well as combinations thereof. In one embodiment said LCO comprises thiophene monomers and/or thiophenes monomers having one or more functional groups or side chains. In another embodiment said functional groups or side chain(s) is/are selected from the group consisting of carboxylic acids, acetic acids, propionic acids, amino acids, amino acid derivatives, neurotransmitters, monosaccharides, polysaccharides, nucleic acids and derivatives as well as combinations thereof. The present invention is however not to be seen as limited by these functional groups or side chain(s), other variants are possible. In another embodiment said LCO comprises at least one thiophene-mer and said thiophene-mer is exchanged with other heterocyclic mers, selected from the group consisting of indole, selenophene, thioazole, phenylene, fluorene, pyrrole, quinoxaline, or benzodithiazole.

The modifications in said LCOs can be in either of the terminals or in the main chain/backbone of the LCO. Examples of heptameric LCOs are h-FTAA, h-HTAA and h-HTA-Glu, and said pentameric LCO is any of p-HTA-His, p-HTA-Lys, p-HTEA, p-HTIm, p-HTA-Tyr, p-HTA-Arg, p-HTA-Asp and p-HTA-Glu. In one embodiment said heptameric LCO is h-FTAA, h-HTAA and h-HTA-Glu, and said pentameric LCO is any of p-HTA-His, p-HTA-Lys, p-HTEA, p-HTIm, p-HTA-Tyr, p-HTA-Arg, p-HTA-Asp and p-HTA-Glu.

In the present invention, a signal is detected on interaction of the LCO with the target, which is a microbial peptide, microbe or compound of microbial origin that may be secreted, located intracellularly or localized to a membrane or cell wall of a microbe. Said method also detects combination of carbohydrate and peptide of microbial origin. The signal can be assessed using different methods. In one embodiment said at least one detected signal is an optical signal, electrical signal, electrochemical signal, or a magnetic signal. In one embodiment the detection signal is a combination of at least two of the signals in the group consisting of optical signal, electrical signal, electrochemical signal, and magnetic signal. In another embodiment said detection signal is an optical signal, such as fluorescence or colorimetric signal; an electrical signal with detection based on electrical properties such as conductivity, resistivity or permittivity; an electrochemical signal with detection based on electrochemical properties, such as charge storage capacity, impedance and redox potential; or a magnetic signal as detected in Hall effect-based and coil-based magnetic detectors or a combination thereof. Once at least one signal is obtained it may be further analysed and compared with the earlier obtained signals from earlier interactions between the target and a LCO. These signals may be archived as a database that may be assessed remotely. The present invention is however working regardless of how the data in the comparative database was collected. Said method is robust and enables distinguishing between microbial peptides, compounds of microbial origin, and one microbe from other. The microbes, compounds of microbial origin, or microbial peptides that can be detected using the present invention method are bacteria, virus, algae or fungi. In one embodiment a method for detection, identification, and/or quantification of microbial peptides from bacteria, virus, algae, or fungi is described. In another embodiment the method is able to discriminate between at least two different microbes, microbial peptides, compounds of microbial origin, bacteria, virus, algae or fungi. Said method provides an opportunity to distinguish between a Gram-negative and Gram-positive bacteria. In one embodiment said method discriminates between Gram-positive and Gram-negative bacteria. In one embodiment said method detects, identifies and/or quantifies at least one of *Firmicutes, Proteobacteria, Chlamydiae, Actinobacteria* and *Spirochaetes*. In one embodiment said method detects, identifies and/or quantifies fragments of viral proteins as peptides. In another embodiment the method is able to discriminate between *Firmicutes* and *Proteobacteria*. Peptides of interest where said method may detect, identify and/or quantify microbes or microbial peptides are structural peptides such as stem peptides and linker peptides or bridge peptides, antimicrobial peptides such as bacteriocins, signalling peptides such as quorum sensing molecules e.g. the staphylococcal quorum sensing peptide autoinducing peptide (AIP). In this case, signalling peptides can be either regulatory and/or secreted.

In one embodiment said method detects, identifies and/or quantifies bacteria of a genus selected from the group consisting of *Bordetella, Borrelia, Brucella, Campylobacter, Escherichia, Francisella, Haemophilus, Helicobacter, Legionella, Leptospira, Neisseria, Pseudomonas, Rickettsia, Salmonella, Shigella, Shewanella, Ureaplasma, Treponema, Vibrio, Yersinia, Streptococcus, Chlamydia, Clostridium, Corynebacterium, Enterococcus, Listeria, Staphylococcus, Micrococcus, Candida, Mycobacterium* or *Mycoplasma*. The present invention is however not to be seen as limited by these bacteria, others are thinkable. The said method preferably detects, identifies, quantifies or diagnose bacteria selected from the group consisting of, *Bordetella pertussis, Borrelia burgdorferi, Brucella abortus, Brucella canis, Brucella melitensis, Brucella suis, Campylobacter jejuni, Candida albicans, Candida glabrata, Escherichia coli, Francisella tularensis, Haemophilus influenzae, Helicobacter pylori, Legionella pneumophila, Leptospira interrogans, Micrococcus luteus, Neisseria gonorrhoeae, Neisseria meningitides, Pseudomonas aeruginosa, Rickettsia rickettsii, Salmonella enteritidis, Salmonella typhi, Salmonella typhimurium, Shigella sonnei, Treponema pallidum, Vibrio cholerae, Yersinia pestis, Clostridium botulinum, Clostridium difficile, Clostridium perfringens, Clostridium tetani, Corynebacterium diphtheriae, Enterococcus faecalis, Enterococcus faecum, Listeria monocytogenes, Staphylococcus aureus, Staphylococcus epidermidis, Staphylococcus saprophyticus, Streptococcus agalactiae, Streptococcus pneumoniae, Streptococcus pyogenes, Chlamydia pneumoniae, Chlamydia psittaci, Chlamydia trachomatis, Mycobacterium leprae, Mycobacterium tuberculosis* and *Mycoplasma pneumoniae*.

In another embodiment the LCOs used in the present invention are in an immobile format. The interaction between LCOs and said object, sample or substance may be in the forms of liquid:liquid, liquid:solid, solid:liquid and/or solid:solid interactions. In one embodiment the method may be run continuously. In one embodiment the LCOs are arranged in a fixed manner on a surface and wherein said sample, object or substance is allowed to pass and react with the LCOs in a continuous flow; or said sample is arranged in a fixed manner on a surface and wherein the LCOs are allowed to pass and come in contact with the sample in a continuous flow. One example of the present invention method, wherein the LCOs are arranged in a fixed manner on a surface and wherein said sample, object or substance is allowed to pass and come in contact with the LCOs in a continuous flow, may be in a catheter tube. Another alternate arrangement can be wherein the said sample, object or substance is arranged in a fixed manner on a surface and the LCOs are allowed to pass and come in contact with the sample, object or substance in a continuous flow. When the sample, object or substance is allowed to come in contact with the LCOs, any type of chemical interaction is thinkable such as, but not limited to Van der Waal binding, hydrogen bonding, hydrophobic and electrostatic interactions, and covalent interactions.

In one embodiment the LCO comprise at least one spacer. In another embodiment the spacer is selected from the group consisting of polyethylene glycol, polyvinyl alcohol, polyacrylic acid, polymethacrylic acid, polyacrylamide and polyvinyl pyrrolidone. The LCOs are in one embodiment attached to the surface through at least one spacer. The present invention is however not to be seen as limited by these spacers, others are possible.

In one embodiment the LCOs are linked to at least one organic or inorganic material comprised of one or more selected from the group consisting of metal, semiconductor material and polymer compound. In one embodiment the LCOs are linked to a nanoparticle comprised of one or more selected from the group consisting of metal, semiconductor material and polymer compound.

In one embodiment the method according to the present invention may be for the collection or removal of LCOs in all fore-mentioned forms from a sample or object. In one embodiment the method is adapted for removal or collection of probes. One possible area of interest is sample collection/concentration when LCOs are conjugated to carriers or nanoparticles.

One aspect of the invention is a kit comprising the LCO as mentioned previously, and instructions for its use in detection, identification, and/or quantification of one or more microbes, microbial peptides or compounds of microbial origin and diagnosis of infection. In one embodiment the kit may be in the form of, but not limited to an emulsion e.g. a cream, a lotion, an ointment, or a textile e.g. a band aid, a pad, clothing, or surface bound e.g. fixed in a tube, a dish, a flask or similar means; fixed to a multiwell plate, fixed to metal surface or in solution e.g. a spray, a vial, a liquid etc. In yet another embodiment the present invention provides a kit or a commercial package comprising the LCOs to detect, identify, or quantify microbial peptides and microbes along with known binding targets of the LCOs, and instructions for the use of the package contents as a test reference for calibration purposes. The kit can also be used for different purposes including but not limited to education or training.

In still another embodiment the present invention provides a user interface to organize, and/or perform algorithmic/mathematical/statistical transformations of signals collected from LCOs and/or present signals from LCOs to the user. Said user interface may additionally comprise data export functions and data comparison functions. Said data export functions and data comparison function may allow for gathered data to be exported and then compared to known data in said database containing knowledge of LCO interactions. The interface has database archived or accesses database remotely.

Another aspect of the invention relates to a computer program product comprising a computer-readable storage medium with instructions adapted to carry out the analysis previously mentioned, preferably statistical analysis, preferably ratio analysis or multivariate analysis, e.g. cluster analysis, principle component analysis (PCA), factor analysis, and hierarchical clustering, when executed by a device having processing capability. In another embodiment said computer program product is adapted to perform ratio analysis or multivariate analysis on obtained results.

In another embodiment said multivariate analysis is selected from the group consisting of PCA and hierarchical clustering. In one embodiment the analysis could be a form of machine learning. In one embodiment machine learning is regression methods, preferably linear discriminant analysis. In another embodiment the computer program product comprises a computer-readable storage medium with instructions adapted to carry out algorithmic/mathematical/statistical transformations of detection signals collected from samples contacted with LCOs and/or present detection signals from samples contacted with LCOs to the user, wherein said computer program product preferably comprise:
a''') Data export functions
b''') Data comparison functions to databases containing data of LCOs interactions according to the present invention; and
c''') Functions for plotting graphs and/or data presentation.

Another aspect of the present invention relates to the use of at least one LCO for detection, identification, and/or quantification of one or more microbes, microbial peptides, or compounds of microbial origin and for diagnosis of an infection.

EXAMPLES

Example 1: Detection of Microbial Peptides a. Detection of Microbial Peptide and Distinction Between Two Microbial Peptides.

Figure 1:
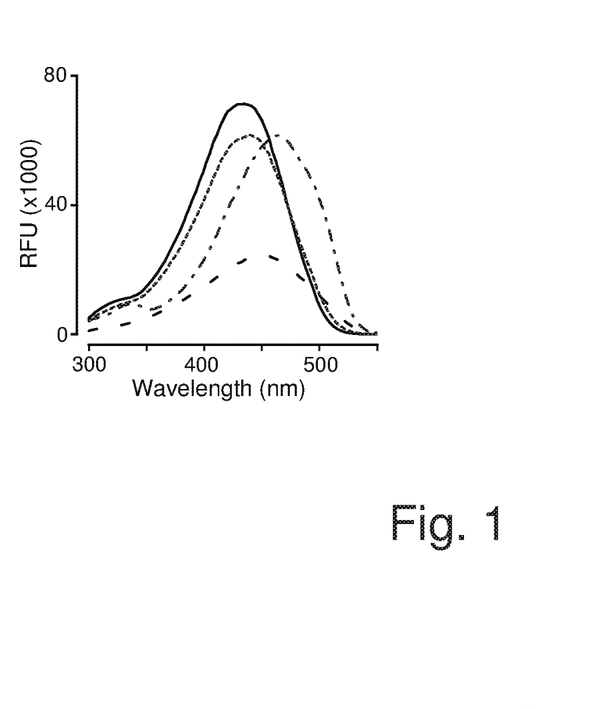
FIG. 1: Detection of microbial peptide and discrimination between two microbial peptides from *Staphylococcus aureus* (*S. aureus*) using LCO probe h-HTA-Glu.

Tubes containing 1 ml i) *S. aureus* stem peptide (Sigma, 2 mM in 30% v/v acetonitrile/PBS); ii) *S. aureus* pentaglycine peptide (Sigma, 2 mM in 100% v/v formic acid/PBS); cells of *S. aureus* strain 8325-4 (Novick, R. 1967 Virology. 33:1, p 155-66) in PBS (prepared by centrifugation of 1 ml overnight culture in Tryptic Soy Broth (TSB)); and iv) PBS, pH 7.4 were prepared. FIG. 1 shows excitation spectra (300-550 nm) recorded after addition of h-HTA-Glu (3 µM final concentration) to extracted stem peptide (- · -), extracted pentaglycince peptide (——), *S. aureus* cells (- - -) and PBS (----). Compared to the PBS control, the stem peptide, the pentaglycine peptide, and intact *S. aureus* cells all showed altered optical signatures, which can be used to discriminate between the different microbial peptides. RFU=relative fluorescence units.

b. Detection of Microbial Peptidoglycan and Discrimination Between Peptidoglycan From Two Gram-Positive Microbial Species.

Figure 2:
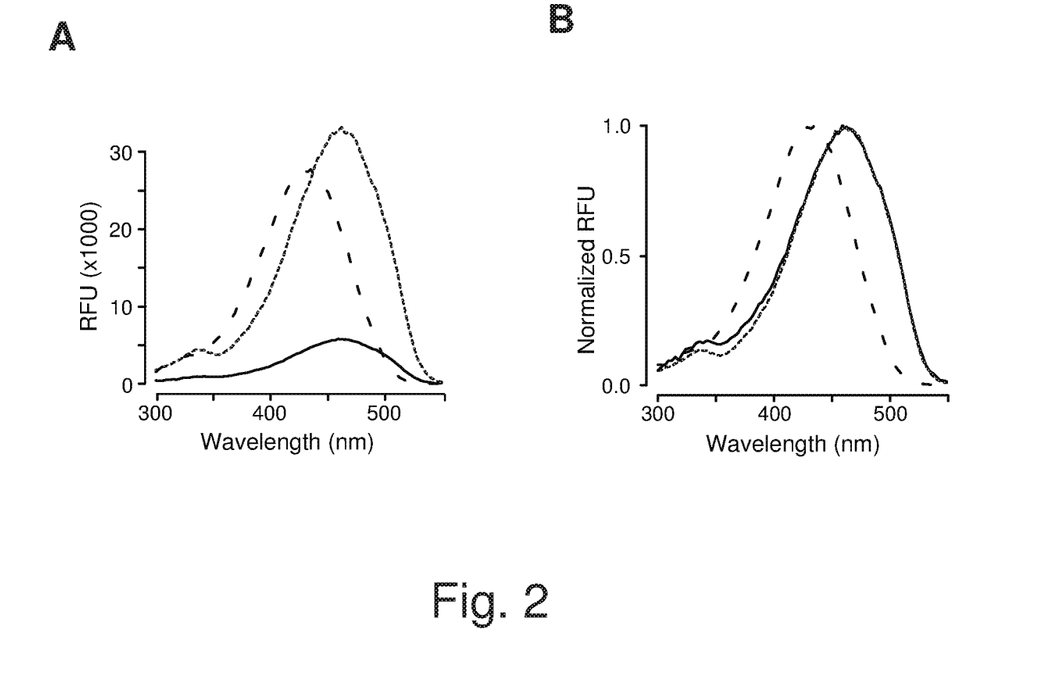
FIG. 2: Detection of microbial peptidoglycan and discrimination between peptidoglycan from two Gram-positive microbial species using LCO probe h-HTA-Glu.

Frozen tubes containing 1 ml suspension (1 mg/ml) of peptidoglycan extracted from *S. aureus* (Sigma) and *M. luteus* (Sigma) were thawed. After addition of h-HTA-Glu (3 µM final concentration), tubes were incubated (37° C., 1 h) before excitation spectra (300-550 nm) were recorded (FIG. 2A). The peak RFUs for h-HTA-Glu mixed with peptidoglycan from *S. aureus* (----) and *Micrococcus luteus* (*M. luteus*) (——) differed distinctly from each other and from the negative control (3 µM h-HTA-Glu in distilled water) (- - -). By plotting the normalized spectra, setting the maximum value of each spectrum to 1.0, the altered nature of spectra from peptidoglycan from *S. aureus* and *M. luteus* compared to the negative control was apparent (FIG. 2B). The fluorescence spectra thus provide methods for discrimination of peptidoglycan from different species.

c. Detection of Microbial Peptide From Gram-Negative Bacteria.

Figure 3:
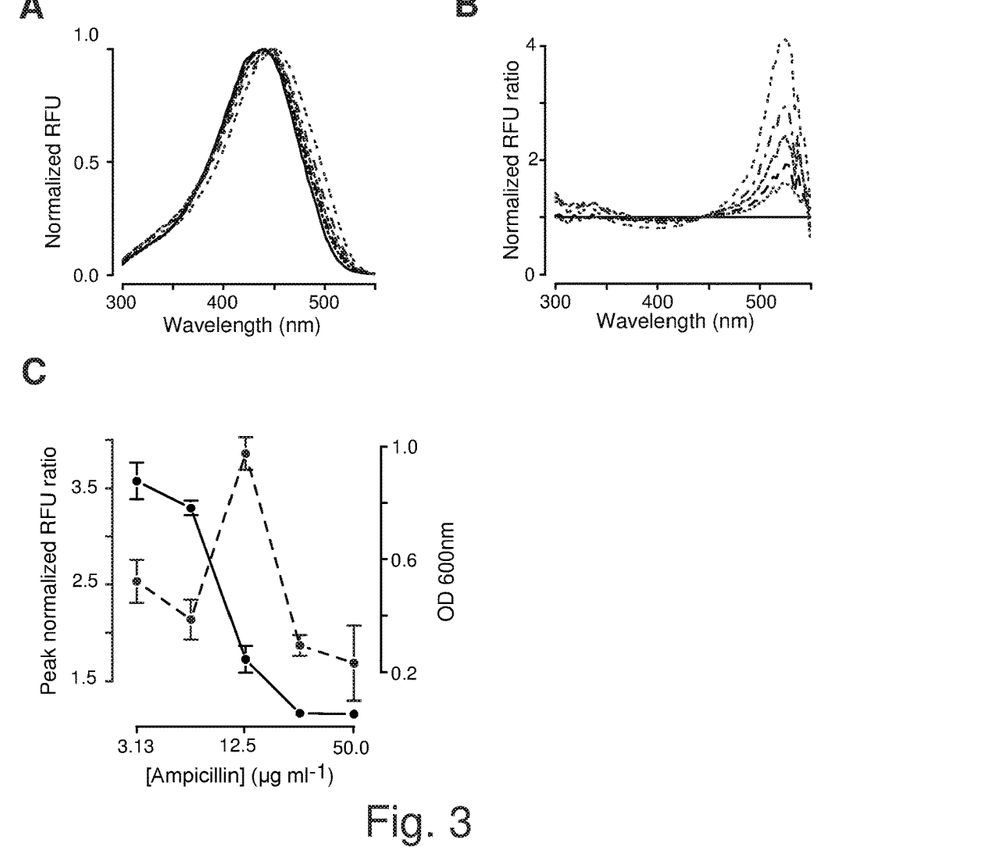
FIG. 3: Detection of microbial peptide from peptidoglycan in Gram-negative bacteria using LCO probe h-HTA-Glu.

Whereas the cell wall of Gram-positive bacteria serves as an excellent source for extraction of peptidoglycan peptides, the thin peptidoglycan layer in the periplasm of Gram-negative bacteria is not readily available for purification. In the absence of commercially available peptidoglycan from Gram-negative bacteria, treatment with ampicillin can be used to alter peptidoglycan structure due to its effect on peptidoglycan peptide cross-linking. This experiment utilises *Escherichia coli* (*E. coli*) bacteria, untreated or treated with different concentrations of ampicillin to represent normal and altered peptidoglycan structures, to analyse whether h-HTA-Glu binds i) Gram-negative bacteria and ii) to peptidoglycan peptides from Gram-negative bacteria. Serial dilutions (1:1 in 100 µl LB medium) starting from 100 µg/ml ampicillin (Sigma) were prepared in a 96-well plate. To each well, 100 µl of an overnight culture of *E. coli* isolate No. 12 (obtained from a child with pyelonephritis at Karolinska University Hospital, published in Kai-Larsen et al. 2010 PLoS Pathogens 6:7, e1001010) diluted 1:50 v/v in LB containing 6 µM h-HTA-Glu, was added. The dilution effect of adding *E. coli* to the ampicillin in the 96-well plate gave a maximum ampicillin concentration of 50 µg/ml. A blank (100 µg/ml ampicillin in LB containing 3 µM h-HTA-Glu, no bacteria) was also included. After incubation at 37° C. for 20 h, excitation spectra (300-550 nm) were recorded. FIG. 3A shows the normalized excitation spectra of h-HTA-Glu mixed with *E. coli* cells subjected to 50 µg/ml (·····) 25 µg/ml (- -), 12.5 µg/ml (·· ··), 6.25 µg/ml (----) and 3.13 µg/ml (- -) ampicillin, as well as the blank (——). The shifts of excitation peaks towards longer wavelengths show that h-HTA-Glu is able to bind to *E. coli* bacteria.

To obtain more detailed information, the variation of the shifts were quantified by plotting each point in the normalised spectrum divided by the corresponding point in the blank (FIG. 3B). The transformed plot shows normalized RFU ratios for *E. coli* bacteria exposed to different concentrations of ampicillin, with 12.5 µg/ml giving the maximum signal. As the peptidoglycan structure is altered by ampicillin, and the normalized RFU ratio changes at different ampicillin concentrations, this experiment shows that h-HTA-Glu binds to the *E. coli* peptidoglycan.

The killing effect of ampicillin is shown in FIG. 3C, with bacterial growth (——) plotted against increasing concentrations of ampicillin. At antibiotic concentrations low enough to allow bacterial growth, the peak normalised RFU ratio (- -), obtained from plotting the maximum normalized RFU ratio from each curve in (B) against respective ampicillin concentration, is 2.5 times higher than the blank. This confirms binding of h-HTA-Glu to *E. coli* bacteria. Interestingly, the increase at 12.5 µg/ml occurs as the optical density is falling. This represents an intermediate state when the peptodoglycan is significantly altered by the antibiotic, but not enough to kill the bacterium. Collectively, these experiments illustrate the ability of LCOs to bind peptidoglycan peptides from Gram-negative bacteria. RFU=Relative fluorescence units, OD=optical density, error bars=standard deviation from 3 experiments. The x-axis in FIG. 3C is logarithmically scaled.

d. Detection of Fungi.

Figure 4:
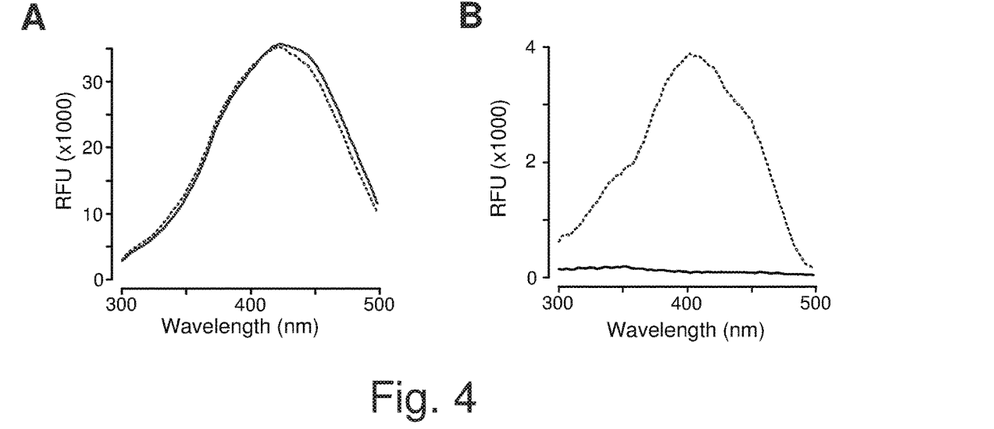
FIG. 4: Detection of fungi using LCO probe p-HTEA.

To analyze the use of LCOs for fungal detection, p-HTEA (3 µM final concentration) was added to 2 ml Yeast Potato Dextrose (YPD) medium containing 1% v/v inoculum of an overnight culture of *Candida albicans* (*C. albicans*, ATCC strain MYA-2876). After vortexing, 200 µl aliquotes were transferred to a 96-well plate, along with a negative control (YPD with 3 µM p-HTEA, no *C. albicans*). The plate was incubated in humidified atmosphere at 37° C., 48 h, when the excitation spectrum (300-500 nm) was recorded. FIG. 4A shows a small yet distinct spectral shift of p-HTEA mixed with *C. albicans* in YPD (·····) compared to YPD with no fungi (——). Next, the medium was carefully removed from each well, not to disturb the fungal cell layer, and 200 µl human blood/well was added, except for the positive control that received fresh YPD medium. The excitation spectrum was again recorded. FIG. 4B shows a significant signal from p-HTEA mixed with *C. albicans* in blood (·····) whereas the signal from p-HTEA in blood with no *C. albicans* (——) was very low. Collectively, this demonstrates the use of the LCO p-HTEA to detect the yeast *C. albicans* under laboratory conditions and with human samples.

Figure 5:
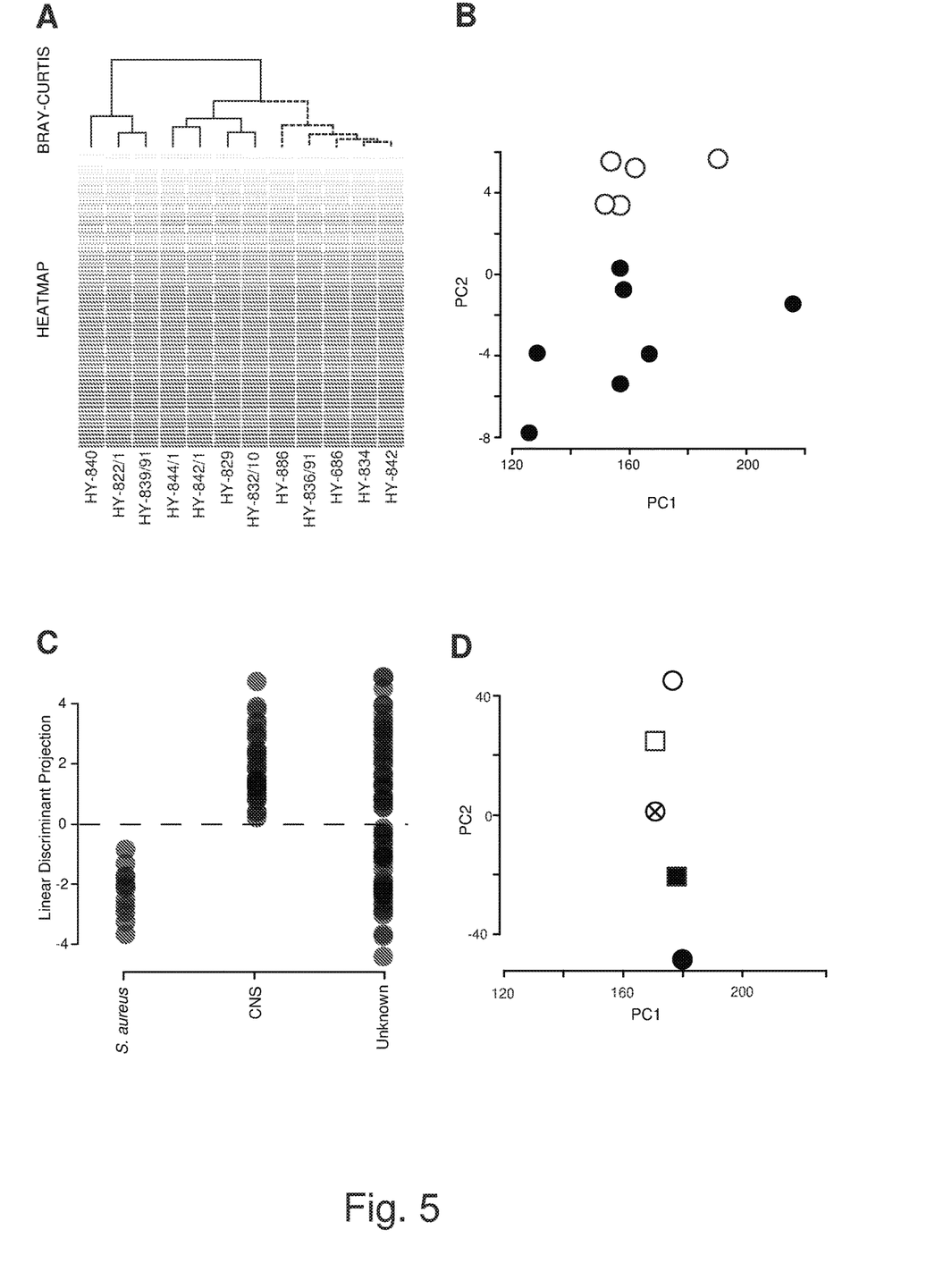
FIG. 5: Detection and identification of multiple bacterial species using the LCO probe h-HTA-Glu.

Example 2: Detection and Identification of Multiple Bacterial Species for Diagnostics Use of LCOs for detection and identification of bacterial strains was demonstrated using isolates of closely related *Staphylococci* species. 100 µl from overnight cultures in Tryptic Soy Broth (TSB, Sigma) of clinical isolates of *S. aureus* (strains HY-886, HY-836/91, HY-686, HY-834, HY-842) and *Staphylococcus epidermidis* (*S. epidermidis*, strains HY-840, HY-822/1, HY-839/91, HY-844/1, HY-842/1, HY-829, HY-832/10) obtained from the Karolinska University Hospital, were diluted in 10 ml TSB, then dispensed in 1 ml aliquots in tubes, to which h-HTA-Glu was added to a final concentration of 2 µM. After mixing, 200 µl of each culture was added in triplicate to a 96-well plate, which was incubated at 37° C., 18-24 h, before excitation spectra (300-550 nm) were recorded. FIG. 5A shows a heatmap representation and Bray-Curtis Hierarchical clustering analysis of the excitation spectra, the latter clearly discriminating between the two *Staphylococci* species with *S. epidermidis* strains clustering to the left (——) and *S. aureus* strains to the right (----). FIG. 5B shows a Principal Component Analysis (PCA) of excitation spectra, revealing clustering of *S. aureus* (○) strains in the upper part and *S. epidermidis* (●) strains in the lower part of the graph. Hierarchical clustering analysis and PCA thus represents two independent analytical methods for LCO-based bacterial species discrimination. FIG. 5C shows that machine learning can be used to predict the identification of unknown bacterial strains isolated from hospitalised patients. The Linear Discriminant Prediction derived from a machine learning process is displayed for known *S. aureus* strains and known coagulase negative staphylococci (CNS) strains. When the Linear Discriminant Prediction derived from a machine learning process of unknown strains was added to the same graph as *S. aureus* and CNS, we found unknown strains with a positive Linear Discriminant Projection, which were classified as CNS strains, and strains having a negative Linear Discriminant Projection, which were classified as *S. aureus*.

To demonstrate the use of LCOs for identification of bacterial strains in mixed samples, overnight cultures of *S. aureus* strain HY-834 and *S. epidermidis* strain HY-840 were mixed at ratios 100:0 (●), 75:25 (■), 50:50 (⊗), 25:75 (□), and 0:100 (○), and h-HTA-Glu (3 µM final concentration) was added. After incubation at 37° C., 30 min, 200 µl of each sample was transferred to a 96-well plate. Excitation spectra (300-550 nm) were recorded and PCA analysis was performed. FIG. 5D shows the sample with pure *S. aureus* located to the bottom of the PCA graph. With increasing amounts of *S. epidermidis* in the mixed cultures, the points moved upwards along the PC2 axis in a predictable pattern, reaching the top position in the pure *S. epidermidis* sample. This demonstrates the feasibility of h-HTA-Glu to identify bacteria present in a mixed sample, and to determine their relative concentration.

Example 3: Detecting Variants of One Bacterial Strain

Figure 6:
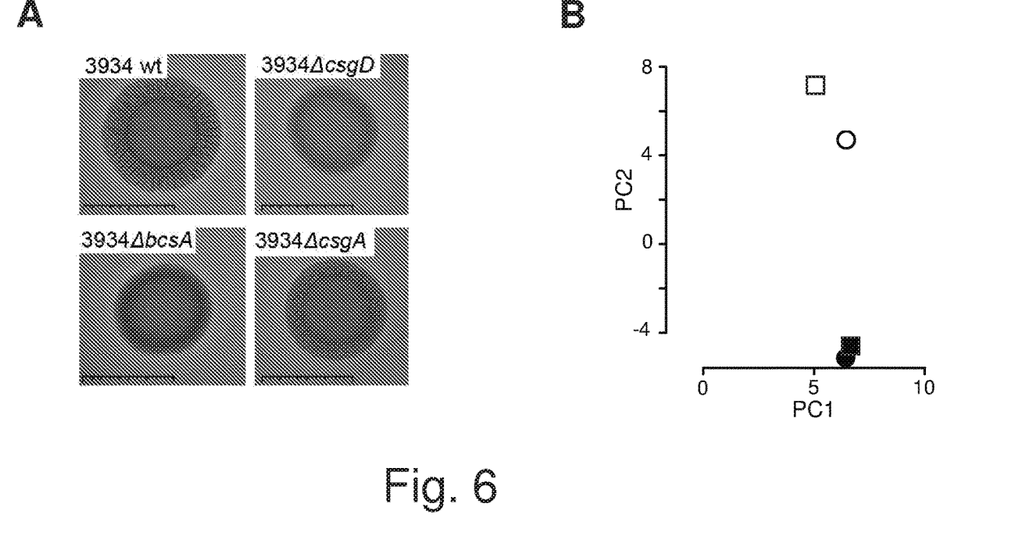
FIG. 6: Detection of variants of one bacterial strain of *Salmonella enteritidis* (*S. enteritidis*) using the LCO probe h-FTAA.

Due to genetic deviations, numerous variants of one bacterial strain exist. These strains, which have identical genotypes except for defined mutations in specific genes, show different expression pattern of proteins, microbial compounds, and virulence factors, which may profoundly influence the pathophysiology of infection. FIG. 6A shows the red, dry and rough (rdar) colony morphology of *Salmonella enteritidis* (*S. enteritidis*) strain 3934 (Solano et al. 1998 J Clin Microbiol. 36(3):674-8) observed on Congo red-containing LB agar plates without salt incubated at 28° C. This is a characteristic morphology of bacteria expressing curli and cellulose. Mutant strains unable to express curli (3934 ΔcsgA), cellulose (3934 ΔbcsA) or both (3934 ΔcsgD) (Latasa et al. 2005 Mol Microbiol. 58(5):1322-39), show distinctly different colony morphology.

To test whether LCOs can be used for identification of the four different strains, colonies of each strain grown on Luria-Bertani (LB) agar plates without salt for 48 h at 28° C. were harvested using a sterile loop, and resuspended in 0.5 ml PBS, pH 7.4. Suspensions were sonicated, then diluted to approximately OD600=0.2 in PBS. 180 µl aliquotes of each suspension were transferred to a 96-well plate and 20 µl h-FTAA (1 µM final concentration) was added to each well. A negative control (PBS with h-FTAA, no bacteria) was also included. Excitation spectra (300-600 nm) were recorded, and data collected in the 450-520 nm interval was subjected to PCA analysis. FIG. 6B shows that strains lacking cellulose production (3934 ΔbcsA (■), 3934 ΔcsgD (●)) cluster at the bottom of the graph, whereas cellulose-producing strains (3934 (○), and 3934 ΔcsgA (□)) located at the top of the graph. Collectively, this demonstrates the use of LCOs to phenotypically differentiate strains of the same species, and to predict/define proteins, microbial compounds, and virulence factor expression.

The invention claimed is:

1. Method for identification, and optional quantification of one or more microbial peptides, comprising the steps of:
   (a). contacting an object, a substance, or a sample with a luminescent conjugated oligothiophene (LCO), wherein said LCO is a tetrameric to 15-meric LCO and at least one of the thiophene-mers is/are exchanged with another heterocyclic mer selected from the group consisting of indole, selenophene, thioazole, phenylene, fluorene, pyrrole, quinoxaline, and benzodithiazole;
   (b). detecting one or more signals of the luminescent conjugated oligothiophene (LCO) of a), of which one or more such signals is indicative of a said microbial peptide; and
   (c). based on said detected one or more signals in b), determining the identity, and optionally the quantity of the one or more microbial peptides on said object or in said substance or sample.

2. Method for the identification of infection causative one or more microbes based on the detection of microbial peptides, comprising the steps of:
   (a'). contacting an object, a substance, or a sample containing said peptides with a luminescent conjugated oligothiophene (LCO), wherein said LCO is a tetrameric to 15-meric LCO and at least one of the thiophene-mers is/are exchanged with another heterocyclic mer selected from the group consisting of indole, selenophene, thioazole, phenylene, fluorene, pyrrole, quinoxaline, and benzodithiazole;
   (b'). detecting at least one signal of the luminescent conjugated oligothiophene (LCO) of a'). of which one or more such signals is indicative of a said microbial peptide; and
   (c'). identifying the causative microbe by comparing said detected at least one signal obtained in b') with a database to identify the causative microbe, wherein said database comprises data from detected signals of previously known samples of microbial peptides.

3. Method according to claim 1 or 2, wherein the luminescent conjugated oligothiophene (LCO) has been bound to or is in contact with a microbial peptide which LCO binding or contact produces a unique signal that can be compared to a database for identification and diagnosis of infection.

4. Method according to claim 2, wherein the database comprises data from samples earlier obtained of microbial peptides, wherein said data comprises detection signals of said samples earlier obtained of at least one microbial peptide wherein said data is an average of more than one sample earlier obtained or data of a single sample.

5. Method according to claim 1 or 2, further comprising the steps:
    (a"). comparing said at least one detected signal of the object, substance or sample to a database comprising data of detected signals of known samples;
    (b"). statistical analysis of said detected signal in relation to data of previous samples in said database; and
    (c"). said identification and/or quantification based on results obtained from step (b").

6. Method according to claim 1 or 2, wherein said luminescent conjugated oligothiophene (LCO) is a pentameric or heptameric luminescent conjugated oligothiophene (LCO).

7. Method according to claim 1 or 2, wherein said luminescent conjugated oligothiophene (LCO) comprises thiophene monomers and/or thiophene monomers having one or more functional groups or side chains.

8. Method according to claim 7, wherein said functional groups or side chain(s) is/are selected from the group consisting of carboxylic acids, acetic acids, propionic acids, amino acids, amino acid derivatives, neurotransmitters, monosaccharides, polysaccharides, nucleic acids and derivatives as well as combinations thereof.

9. Method according to claim 1 or 2, wherein said at least one detected signal is an optical signal, an electrical signal, an electrochemical signal, or a magnetic signal.

10. Method according to claim 1 or 2, for identification and/or quantification of microbial peptides from bacteria, virus, algae or fungi.

11. Method according to claim 1 or 2, wherein the method is able to discriminate between at least two different microbes, or microbial peptides, bacteria, virus, algae or fungi.

12. Method according to claim 1 or 2, wherein said method is able to discriminate between Gram-positive and Gram-negative bacteria.

13. Method according to claim 1 or 2, wherein said method identifies and/or quantifies at least one of *Firmicutes, Proteobacteria*, Chlamydiae, Actinobacteria and *Spirochaetes*.

14. Method according to claim 1 or 2, wherein the method is able to discriminate between *Firmicutes* and *Proteobacteria*.

15. Method according to claim 10, wherein said method identifies and/or quantifies bacteria of a genus selected from the group consisting of *Bordetella, Borrelia, Brucella, Campylobacter, Escherichia, Francisella, Haemophilus, Helicobacter, Legionella, Leptospira, Neisseria, Pseudomonas, Rickettsia, Salmonella, Shigella, Shewanella, Ureaplasma, Treponema, Vibrio, Yersinia, Streptococcus, Chlamydia, Clostridium, Corynebacterium, Enterococcus, Listeria, Staphylococcus, Micrococcus, Candida, Mycobacterium* or *Mycoplasma*.

16. Method according to claim 10, wherein said method identifies and/or quantifies bacteria selected from the group consisting of *Bordetella pertussis, Borrelia burgdorferi, Brucella abortus, Brucella canis, Brucella melitensis, Brucella suis, Campylobacter jejuni, Candida albicans, Candida glabrata, Escherichia coli, Francisella tularensis, Haemophilus influenzae, Helicobacter pylori, Legionella pneumophila, Leptospira interrogans, Micrococcus luteus, Neisseria gonorrhoeae, Neisseria meningitides, Pseudomonas aeruginosa, Rickettsia rickettsii, Salmonella enteritidis, Salmonella typhi, Salmonella typhimurium, Shigella sonnei, Treponema pallidum, Vibrio cholerae, Yersinia pestis, Clostridium botulinum, Clostridium difficile, Clostridium perfringens, Clostridium tetani, Corynebacterium diphtheriae, Enterococcus faecalis, Enterococcus faecum, Listeria monocytogenes, Staphylococcus aureus, Staphylococcus epidermidis, Staphylococcus saprophyticus, Streptococcus agalactiae, Streptococcus pneumoniae, Streptococcus pyogenes, Chlamydia pneumoniae, Chlamydia psittaci, Chlamydia trachomatis, Mycobacterium leprae, Mycobacterium tuberculosis* and *Mycoplasma pneumoniae*.

17. Method according to claim 1 or 2, wherein at least one or all steps is/are or are carried out in vivo, in vitro or in situ.

18. Method according to claim 1 or 2, wherein the method may be run continuously.

19. Method according to claim 5, wherein the analysis of step b" is conducted on a computer configured to perform ratio analysis or multivariate analysis or machine learning on obtained results.

20. Method according to claim 19, wherein said basic multivariate analysis is selected from the group consisting of principle component analysis (PCA) and hierarchical clustering; and/or machine learning is regression methods, preferably linear discriminant analysis.

* * * * *